United States Patent [19]

Bonucci

[11] Patent Number: 4,630,393

[45] Date of Patent: Dec. 23, 1986

[54] PRODUCTION OF HYBRID "IMPROVED SUPERSWEET" SWEET CORN

[75] Inventor: Peter A. Bonucci, Northfield, Minn.

[73] Assignee: UF Genetics, Inc., Hollister, Calif.

[21] Appl. No.: 789,930

[22] Filed: Oct. 22, 1985

Related U.S. Application Data

[63] Continuation of Ser. No. 653,446, Sep. 21, 1984.

[51] Int. Cl.$^4$ .............................................. A01G 1/00
[52] U.S. Cl. .................................. 47/58; 47/DIG. 1
[58] Field of Search ........................ 47/1, 58, DIG. 1

[56] References Cited

U.S. PATENT DOCUMENTS 3,971,161  7/1976  Bonucci ................................. 47/58
4,051,629 10/1977  Galinat .................................. 47/58

OTHER PUBLICATIONS

Rosenbrook et al. (1971) Crop Science 11:536-538.
Holder et al. (1974) Crop Science 14:647-648 and 14:643-646.

Primary Examiner—Robert E. Bagwill
Attorney, Agent, or Firm—Robert P. Blackburn; Ellen P. Winner; Lorance L. Greenlee

[57] ABSTRACT

A new method of combining the genetic mutants $su_1$ and $sh_2$ to produce sweet corn having an unusually high sugar content.

8 Claims, No Drawings

PRODUCTION OF HYBRID "IMPROVED SUPERSWEET" SWEET CORN

This application is a continuation of application Ser. No. 653,446, filed 9/21/84.

FIELD OF THE INVENTION

Sweet corn is widely used for human consumption throughout the world. The majority of the commonly used sweet corn hybrids in the United States are single crosses involving the suHd 1 (sugary-1) in combination with other genes that increase sugar content and/or improve quality. The recessive $su_1$ gene was first described in 1911 (East, E. M. and H. K. Hayes (1911) Conn. Agric. Expt. Stn. Bull. 167:142pp.) as an allele of the dominant $Su_1$ gene which is field corn, or sometimes called dent corn. The effects of the genes shrunken-2 ($sh_2$) and $su_1$ on the distribution of endosperm carbohydrates have also been studied (Laughnan, J. C. (1953) Genetics 38:485–499). It was found that the almost 20% of the dry weight of the $sh_2Su_1$ kernels was composed of sugars. The $sh_2Su_1$ kernels showed a decrease in the accumulation of water soluble polysaccharides. The "Supersweet" hybrids ($Su_1Su_1sh_2sh_2$) are referred to as sweetcorns because of their high sugars, but do not contain the $su_1$ gene. This invention teaches a method whereby the above genetic mutants $su_1$ and $sh_2$ can be combined in a breeding program resulting in a sugar content higher than theoretical expectations and with outstanding sweet corn quality characteristics.

BACKGROUND OF THE INVENTION

The various types of corn (i.e., maize) have widely differing uses because of, inter alia, the widely differing carbohydrate content of the kernels. For example, field corn can be a good livestock feed but is not well suited for human consumption, except as the end result of further processing. Sweet corn, on the other hand, can be highly palatable to humans in the raw state. Sweet corn is more desirable as a vegetable corn because of its relatively higher sugar content, higher water soluble polysaccharides (WSP), lower starches and more tender pericarp in addition to other factors that contribute to "quality" (i.e., appearance both before and after removing the husks). It is the WSP which gives sweet corn kernels their smooth, creamy characteristics which contrast sharply with the gritty, starchy effect experienced when eating field corn. Compared to field corn, elevated sugar levels and WSP as well as reduced starch are the factors that most Americans associate with sweet corn. Supersweets are low in WSP but are not, as a group, particularly starchy.

In the industrial practices of processing vegetables (e.g., canning and freezing), both the WSP level and the sugar level can be important. In a typical canning process, for example, the kernels are removed from the ears of sweet corn and the resulting mass of detached kernels (or "cut") is automatically packaged in cans along with a watery liquor. Most commonly, extraneous natural sweeteners (e.g., sucrose or honey) are added to the liquor to increase the natural sweetness of the sweet corn. It is the experience of most canneries that the normal or natural level of sweetness in sweet corn is not high enough for canning. Therefore, assuming equivalent yield, a hybrid corn which was very high in sugars would be an improvement over normal sweet corn and would facilitate the operations of the canning industry. Also, there may be marketing advantages in a "no additive" canned product. Sugar cannot be added to a frozen whole-ear pack.

In most breeding programs to date, development of supersweet hybrids with high sugar content (e.g., sucrose) has resulted in a product which is below normal sweet corn in WSP content. Some of the more interesting studies to produce high sugar content corn have been carried out with a mutant gene shrunken-2 ($sh_2$). When the genome is homozygous $sh_2sh_2$, the sweetness of the corn is increased and the WSP content is often lowered, but it is felt that the higher sugar levels compensate for the lowered WSP levels. In addition, the endosperm weight and starch levels are reduced, resulting in a light weight, easily damaged seed. Germination of these light weight seeds can be a problem both in inbred production and in hybrid strains. To improve vigor and germination, dent corn (a type of field corn) has been used as the background for the $sh_2$ gene. However, the dominant dent corn genes can necessitate isolation of supersweet hybrids from both field corn and "sugary" sweet corn since cross pollination by any foreign pollen can cause all the kernels to be dent corn in character.

For a review of the effects of genetic interactions of the $sh_2$ gene with other genes (e.g., the $sh_1$ gene) with particular emphasis on investigating carbohydrate composition of the kernels, see: Rosenbrook and Andrews (1971) Crop Science 11:536–538; Holder, Glover and Shannon, (1974) Crop Science 14:647–648 and 14:643–646.

A previous disclosure (U.S. Pat. No. 3,971,161 issued July 27, 1976) has described a particular genetic combination using $su_1su_1sh_2sh_2$. This patent has further described results of some prior studies of the sugary-shrunken genotype. As stated therein, an "apparently unpublished" report detailed some work done on so-called "Ultrasweet" or "Supersweet" sweet corn which was based on the combination of the recessive gene shrunken-2 ($sh_2$) on chromosome 3 with the dominant starchy-1 ($Su_1$) on chromosome 4. The shrunken-sugary combination ($sh_2sh_2su_1su_1$) is also discussed. The $sh_2sh_2su_1su_1$ combination was said to be "defective to the point of being nearly lethal and impossible to produce except in a background of pseudo starchy-sugary". It was further reported that the combination of $sh_2sh_2su_1su_1$ can be commercially produced by having the seventh chromosome of Tripsacum ($Tr_7$) which carries the $Su_1$ allele, "present as an extra pair in the seed parent". The report then goes on to describe a hybrid produced by the cross $sh_2sh_2su_1su_1Tr_7 \times sh_2sh_2su_1su_1$. Thus, in spite of the exceptionally poor seed quality of the homozygous $sh_2sh_2su_1su_1$ (see above), the above quoted report suggests using $su_1$ and $sh_2$ in a homozygous condition. However, it has not been commercially feasible to employ homozygous sugary-shrunken strains on both sides of a cross.

However, production of a hybrid sweet corn has been achieved by use of $su_1$ and $sh_2$ in a particular genetic combination (U.S. Pat. No. 3,971,161, issued July 27, 1976). The parents for the heterozygous F1 ears of this hybrid sweet corn are Sun Seeds proprietary inbred lines and are not well known. These parents are described in the literature. See, for example, the Crop Science articles cited above.

Although normal sweet corn would be used as either the male or the female parent, it was considered preferable in U.S. Pat. No. 3,971,161 to use normal sweet corn as the female parent. The male parent (i.e., still tasseled parent), was a homozygous sugary-shrunken corn. Therefore, using the notations $su_1su_1sh_2sh_2$ to represent the sugary-shrunken parent and $su_1su_1Sh_2Sh_2$ to represent the normal sweet corn parent, the system or method of producing commercial quantities of heterozygous F1 seed can be schematically represented as follows:

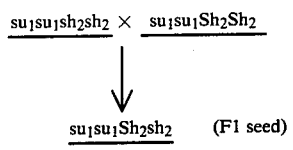

$su_1su_1sh_2sh_2 \times su_1su_1Sh_2Sh_2$ $su_1su_1Sh_2sh_2$ (F1 seed)

The F1 was normal appearing sweet corn seed, but because it was heterozygous for $Sh_2sh_2$, planting and field pollination produced F2 ears characterized by a 3:1 segregation of normal kernels to shrunken ($sh_2sh_2$) kernels. However, phenotypically all kernels appeared the same. Schematically represented, the genetic composition of the triploid (3N) endosperm of these kernels is:

| Genotype | Phenotype | Ratio |
|---|---|---|
| $su_1su_1su_1Sh_2Sh_2Sh_2$ | Sugary | 1 |
| $su_1su_1su_1Sh_2Sh_2sh_2$ | " | 1 |
| $su_1su_1su_1Sh_2sh_2sh_2$ | " | 1 |
| $su_1su_1su_1sh_2sh_2sh_2$ | Sugary, shrunken | 1 |

The homozygous $sh_2$ kernels increased the average sugar content of the "cut" while the normal sweet corn kernels maintained the average WSP at a high level. When a consumer sampled the F2 kernels, only the effects provided by these averages was tasted. It was not apparent that some kernels were relatively lower in WSP and relatively higher in sucrose while other kernels were relatively lower in sucrose and relatively higher in WSP.

The combined effect of 25% high sugar F2 kernels with 75% high WSP F2 kernels was thus very favorable for processing of the "cut". The average content of sucrose, total sugar (i.e., sucrose+fructose+glucose) and WSP in the F2 "cut" on a dry weight basis was also described (U.S. Pat. No. 3,971,161 issued July 27, 1976).

Published data are available for the carbohydrate content of F2 kernels obtained from normal (field) corn, sweet corn, super-sweet corn with a normal (field) corn background, and super-sweet corn with a sweet corn background (see Table below), as well as the individual F2 genotypes $su_1su_1su_1Sh_2Sh_2Sh_2$, $su_1su_1su_1Sh_2Sh_2sh_2$, $su_1su_1su_1Sh_2sh_2sh_2$ and $su_1su_1su_1sh_2sh_2sh_2$ (hereinafter referred to as the "four genotypes"). The following table summarized averages of this published data.

| Various carbohydrates 21 days after pollination (70–76% moisture) as percent dry weight | | | | | |
|---|---|---|---|---|---|
| | | Percent of Dry weight | | | |
| Endosperm Phenotype | Genotype | Sucrose | Total Sugar | WSP | Starch |
| Starchy | $Su_1Su_1Sh_2Sh_2$ | 7.3 | 10.5 | 0.55 | 47.0 |
| Sugary | $su_1su_1Sh_2Sh_2$ | 12.5 | 18.1 | 36.6 | 18.3 |
| Shrunken | $Su_1Su_1sh_2sh_2$ | 26.0 | 32.7 | 0.67 | 17.3 |
| Sugary-shrunken | $su_1su_1sh_2sh_2$ | 39.8 | 44.3 | 7.1 | 2.8 |
| Average of "four genotypes" in 1:1:1:1 ratio | | 19.3 | 24.7 | 29.2 | 14.4 |

Various hybrids have been produced by crosses of the above genotypes. In all these hybrids, the expected sugar content (based on genotype) corresponded to the measured sugar content. These findings correspond to the predicted sugar content based upon the F1 genotype and on the Mendelian ratios of genotypes in the F2 seeds, assuming each genotype contributes a characteristic sugar content to the "cut". For example, a representative sample of "cut" produced by the hybrid described in U.S. Pat. No. 3,971,161 had a sucrose content of 24.7% (percent of dry weight), in close agreement with the calculated value of 19.3%. For crosses involving the sugary and shrunken loci or their wild-type alleles, the experimental values for sugar content in prior art hybrids have corresponded closely with the calculated values. We have discovered a surprising exception to this correspondence and describe in the "Detailed Description of the Invention" a novel category of hybrids in which the sugar content is higher than the theoretical expected on the basis of the parent genotypes.

DETAILED DESCRIPTION OF THE INVENTION

In contrast to the production of sweet corn described in U.S. Pat. No. 3,971,161, issued July 27, 1976, where the F1 seed has the genotype $su_1su_1Sh_2sh_2$, a new set of varieties herein termed "Improved Supersweet" hybrids and exemplified herein by a new variety, "Sweetie" (Trademark Application 73/462333, Agrigenetics Corporation, Boulder, Colo.) has been produced by use of a novel "Improved Supersweet" process where the F1 seed has the genotype $Su_1su_1sh_2sh_2$. The process for producing the variety "Sweetie" differs from that previously used to produce a "Sweet Gene Hybrid" (see U.S. Pat. No. 3,971,161) although both used a sugary-shrunken ($su_1su_1sh_2sh_2$) inbred as one parent. The significant difference, which gave an entirely unexpected result (see below), is that for a "Sweet Gene Hybrid" (Trademark, Agrigenetics Corporation, Boulder, Colo.) a sugary ($su_1su_1Sh_2Sh_2$) inbred was used as the second parent while in the present invention, the new variety Sweetie used a dent shrunken ($Su_1Su_1sh_2sh_2$) inbred as the second parent. The process of producing the "cut" of Sweetie from the seeds of the F2 generation can be schematically represented as follows:

Parents  $Su_1Su_1sh_2sh_2 \times su_1su_1sh_2sh_2$

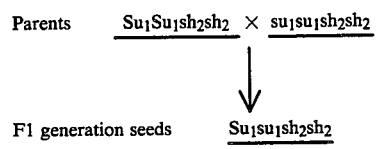

F1 generation seeds  $Su_1su_1sh_2sh_2$

The F1 is homozygous shrunken, but because it is heterozygous for $Su_1su_1$, planting and field pollination produced F2 ears characterized by a 3:1 segregation of dent, shrunken ($Su_1Su_1sh_2sh_2$ and $Su_1su_1sh_2sh_2$) kernels to sugary shrunken ($su_1su_1sh_2sh_2$) kernels (Table 1). Schematically represented, the genetic composition of the triploid (3N) endosperm of these kernels is:

| | Genotype | Phenotype |
|---|---|---|
| Class "Improved | $Su_1Su_1Su_1sh_2sh_2sh_2$ | 3 dent, |
| Supersweet" | $Su_1Su_1su_1sh_2sh_2sh_2$ | shrunken |
| Variety "Sweetie" | $Su_1su_1su_1sh_2sh_2sh_2$ | |
| | $su_1su_1su_1sh_2sh_2sh_2$ | 1 sugary shrunken |

The endosperm becomes triploid by a well-understood process described here briefly. After meiosis and subsequent mitotic divisions and fertilization, there are ten nuclei (8 female and 2 male) within the embryo sac. One of the sperm nuclei fuses with the egg nucleus producing the diploid zygote; and the other sperm nucleus fuses with the two polar nuclei to form a triploid nucleus. While the zygote nucleus begins division to form the new sporophytic embryo, this triploid nucleus undergoes rapid mitosis to form a specialized nutritive tissue, the endosperm. At this point the female antipodal nuclei and synergids simply degenerate.

Since shrunken kernels are known to contain 38.7% sugars, and sugary shrunken is known to contain 47.3% sugars (Table 1), such a 3:1 segregation would be expected to yield a "cut" in the F2 seed generation of 40.8% sugars.

$$\frac{(3 \times 38.7) + (1 \times 47.3)}{4} = 40.8\%$$

The entirely unexpected result was that the sugar content of the F2 seed generation cut was in the region of 50% and there was a slight increase in WSP from 3.25 to 3.92 in one case and from 3.25 to 3.4 in the other ranging from 4–20% increase over the WSP content of $Su_1Su_1sh_2sh_2$. This is a very large reduction from the WSP level of normal sweet corn which is 37%. These experiments have been repeated with consistent results. The reason for such a high sugar content is not apparent. A summary of the two sets of data is given below (Table 1).

TABLE 1

| | | | Total Sugars % of dry yeast | |
|---|---|---|---|---|
| Phenotype | Genotype | Generation | Expected | Observed[d] |
| Shrunken | $sh_2sh_2$ | Parental-1 | | 38.2%; 39.2%[a] |
| Sugary-shrunken | $su_1su_1sh_2sh_2$ | Parental-2 | | 47.3%[b] |
| 75% shrunken | $sh_2sh_2$ | F2 kernels from "Sweetie" made by cross[c] of Parental-1 × Parental-2 | 40.8% | 1st 50.05%; 47.3% field trials |
| 25% sugary-shrunken | $su_1su_1sh_2sh_2$ | | | |
| 75% shrunken | $sh_2sh_2$ | F2 kernels from cross[c] of Parental-1 × Parental-2 | 40.8% | 50.5%; 49.9% 2nd 51.4%; 52.4% field trials 52.0%; 52.8% |
| 25% sugary-shrunken | $su_1su_1sh_2sh_2$ | | | |

[a]Figures obtained by analysis of samples from the variety Florida Staysweet.
[b]Figures obtained by analysis from the variety Ultrasweet S32197.
[c]A cross of Parental-1 × Parental-2 produces the F1 hybrid "Sweetie".
[d]Within any one experiment, the total sugars obtained from the various genotypes and measured as a percent of dry weight, are consistent relative to each other. However, a comparison of different experiments always shows variation of the total sugars within each genotype. Such variation is presumably due to variations in the growing conditions, variations in soil and other variations which are impossible to control between experiments. It is pointed out here that the expected total sugars as a percent of dry weight were obtained by use of the higher values in the range of figures obtained for the parental genotypes. The percentage of sugar as a percentage of dry weight is also shown diagrammatically (FIG. 1).

In addition to the data given above (Table 1), further data on the carbohydrate and sugar contents are given (Table 2). These data show that the high sugar content of Sweetie has not resulted in the appearance of other undesirable features, e.g., high starch content.

TABLE 2

| Phenotype | Genotype | Generation | % dry weight @ harvest | Carbohydrates (% of dry weight) | | | Individual Sugars (% of dry weight) | | |
|---|---|---|---|---|---|---|---|---|---|
| | | | | Sugars | WSP | Starch | Fructose | Glucose | Sucrose |
| Shrunken[a] | $sh_2sh_2$ | Parental-1 | 20.4 | 38.2 | 3.5 | 13.0 | 2.2 | 3.5 | 39.0 |
| | | | 21.6 | 39.2 | 3.0 | 13.8 | 1.5 | 2.6 | 42.9 |
| Sugary, shrunken[b] | $su_1su_1sh_2sh_2$ | Parental-2 | 21.2 | 47.3 | 5.2 | 7.0 | 2.3 | 4.2 | 50.8 |
| 75% dent, shrunken | $sh_2sh_2$ | F2 kernels from cross[c] of Parental-1 × Parental-2 | 21.8 | 50.5 | 3.7 | 8.6 | 3.9 | 5.0 | 51.5 |
| 25% sugary, shrunken | $su_1su_1sh_2sh_2$ | | 22.5 | 47.3 | 3.1 | 10.8 | 2.6 | 3.5 | 47.2 |
| 75% dent, shrunken | $sh_2sh_2$ | F2 kernels from cross of Parental-1 × Parental-2 | 22.0 | 50.5 | 4.0 | 12.0 | 1.8 | 2.5 | 47.1 |
| 25% sugary, shrunken | $su_1su_1sh_2sh_2$ | | 21.7 | 49.9 | 3.8 | 10.4 | | | |
| | | | 22.5 | 51.4 | 4.2 | 11.5 | | | |
| | | | 23.1 | 52.4 | 3.4 | 9.0 | | | |
| | | | 23.9 | 52.0 | 4.8 | 9.4 | | | |

TABLE 2-continued

| Phenotype | Genotype | Generation | % dry weight @ harvest | Carbohydrates (% of dry weight) | | | Individual Sugars (% of dry weight) | | |
|---|---|---|---|---|---|---|---|---|---|
| | | | | Sugars | WSP | Starch | Fructose | Glucose | Sucrose |
| | | | 22.0 | 52.8 | 3.3 | 9.0 | | | |

[a] Figures were obtained by analysis of samples from the variety Florida Staysweet.
[b] Figures were obtained by analysis of samples from the variety Ultrasweet S32197.
[c] A cross of Parental-1 × Parental-2 produces the F1 hybrid "Sweetie".

The first field trials were conducted on "Sweetie" grown in the State of New York while the second field trials were conducted in Florida. The results of these trials were very similar indicating that environmental factors associated with the geographical location was not a major factor in the expression of the "Sweetie" phenotype. The increase in sugar content over the expected value is significant. The hybrids resulting from the described hybridization method are markedly sweeter in taste than hybrids with sugar contents in the expected 40% range. Remarkably, the high sugar content is achieved without sacrificing desirable attributes of texture, creaminess and flavor. The resulting "Improved Supersweet" varieties yield excellent sweet corn whether fresh, frozen or canned.

In addition to the unexpectedy high sugar content of the Sweetie variety, yield in one independent trail was 67 crates per acre higher than the closest competition, namely, the variety "Sweet Time" (Bradenton Agricultural Research and Education Center, IFAS, University of Florida: Research Report BRA 1983-22: November 1983). In a second independent trial the Sweetie variety was third highest in yield. Since the F1 generation seeds have the genotype $Su_1su_1sh_2sh_2$, the seeds appear shrivelled or almost like raisins. These seeds are lighter weight than sugary sweet corn seeds with 3,400–3,900 seeds per pound versus sugary sweet corn at 1,800–2,300 seeds per pound.

The class of Improved Supersweet Corn Hybrids at the eating or processing stage display advantageous handling and storage properties. The extra sweetness and excellent flavor provide that "Improved Supersweets" such as "Sweetie" will hold longer than hybrids in the field, during shipping, and on the produce counter.

EXAMPLE 1

Production of an "Improved Supersweet" Variety of Hybrid Sweet Corn (a) A first row of shrunken sweet corn ($Su_1Su_1sh_2sh_2$) is planted. Any inbred or variety of shrunken may be used.

(b) A second row of sugary-shrunken sweet corn ($su_1su_1sh_2sh_2$) is planted within cross fertilizing distance of the first row. Again, any inbred or variety of sugary-shrunken may be used.

(c) The plants in one of the two rows are functionally emasculated. Functional emasculation is defined here as rendering a plant male sterile and may be achieved in many ways, e.g., by detasseling, by use of gameticides or by use of a cytoplasmic male sterile strain.

(d) The row which is functionally emasculated serves as the female parent and is fertilized by pollen from the other male fertile row to produce an F1 hybrid. Finally the seeds on the ears of the female parent (i.e., ears which develop on the functionally emasculated plants) are harvested. These F1 seeds are then planted and the ears which develop on these F1 hybrids are harvested for consumption.

What is claimed is:

1. A method for producing a hybrid sweet corn comprising the steps of:
   (a) selecting a first shrunken sweet corn homozygous for $sh_2$, wherein said shrunken sweet corn can be genotypically represented as:

$Su_1Su_1sh_2sh_2$;

(b) selecting a second, sugary-shrunken, corn which can be genotypically represented as:

$su_1su_1sh_2sh_2$;

(c) crossing said first corn as either parent with said second corn as the other parent, to produce a hybrid sweet corn which is heterozygous and genotypically represented as:

$Su_1su_1sh_2sh_2$.

2. The method of claim 1 wherein said first corn is used as the female parent.

3. The method of claim 1 wherein said first corn is used as the male parent.

4. The method of claim 1 wherein said hybrid corn is subsequently planted to obtain F2 ears of corn carrying kernels which can be genotypically represented as approximately 25% $Su_1Su_1Su_1sh_2sh_2sh_2$, 25% $Su_1Su_1su_1sh_2sh_2sh_2$, 25% $Su_1su_1su_1sh_2sh_2sh_2$, and 25% $su_1su_1su_1sh_2sh_2sh_2$.

5. The method of claim 4 wherein said kernels are mechanically removed from said F2 ears and processed to provide a processed sweet corn product or whole ears are processed for a frozen product.

6. A processed corn product produced according to the method of claim 5.

7. A hybrid corn plant produced according to the method of claim 4.

8. A hybrid corn seed according to the method of claim 1.

* * * * *